(12) United States Patent
Djeu et al.

(10) Patent No.: US 11,311,336 B1
(45) Date of Patent: Apr. 26, 2022

(54) LASER ENERGY DELIVERY HAND PIECE WITH DISPOSABLE OPTICAL FIBER

(71) Applicants: Derek Djeu, Tampa, FL (US); Nicholas Djeu, Tampa, FL (US)

(72) Inventors: Derek Djeu, Tampa, FL (US); Nicholas Djeu, Tampa, FL (US)

(*) Notice: Subject to any disclaimer, the term of this patent is extended or adjusted under 35 U.S.C. 154(b) by 0 days.

(21) Appl. No.: 17/181,875

(22) Filed: Feb. 22, 2021

Related U.S. Application Data (60) Provisional application No. 62/980,354, filed on Feb. 23, 2020, provisional application No. 63/066,306, filed on Aug. 16, 2020.

(51) Int. Cl.
*A61B 18/22* (2006.01)
*A61B 17/00* (2006.01)
*A61B 18/20* (2006.01)

(52) U.S. Cl.
CPC ...... *A61B 18/22* (2013.01); *A61B 2017/0023* (2013.01); *A61B 2017/00473* (2013.01); *A61B 2017/00862* (2013.01); *A61B 2018/2005* (2013.01); *A61B 2018/2253* (2017.05)

(58) Field of Classification Search
CPC .............. A61B 18/22; A61B 2018/225; A61B 2018/2253; A61B 2018/2255; A61B 2018/2285; A61B 2017/0023; A61B 2017/00234; A61B 2017/0046; A61B 2017/00464; A61B 2017/00463; A61B 2017/00473; A61B 18/2005; A61B 2017/00469
USPC .................................................. 600/1, 13–16
See application file for complete search history.

(56) References Cited

U.S. PATENT DOCUMENTS

| | | | | |
|---|---|---|---|---|
| 5,304,172 A | * | 4/1994 | Manoukian | A61B 18/24 385/60 |
| 5,651,783 A | * | 7/1997 | Reynard | A61B 1/042 606/17 |
| 5,676,678 A | * | 10/1997 | Schad | A61B 17/29 606/170 |
| 6,258,083 B1 | * | 7/2001 | Daniel | A61B 1/00183 606/41 |
| 10,206,744 B2 | * | 2/2019 | Shurgalin | A61B 18/22 |
| 2002/0064328 A1 | * | 5/2002 | Neuberger | A61B 18/22 385/1 |
| 2006/0004348 A1 | * | 1/2006 | Scheller | A61B 18/24 606/4 |

(Continued)

*Primary Examiner* — Ahmed M Farah
(74) *Attorney, Agent, or Firm* — QuickPatents, LLC; Kevin Prince (57) ABSTRACT

A hand piece for delivering energy from a laser to a target through a fiber tip includes an elongated handle having a proximal end and a distal end. An axial bore traverses the handle along a longitudinal axis thereof. A fiber tip holding mechanism is fixed within the axial bore of the handle and includes a forward section fixed with the handle, a spring, and a rear section that includes a hollow collet projecting forward therefrom that traverses the spring and the forward section. The forward section is slidable rearward towards the rear section to compress the spring in a rear position. The spring urges the forward section forward into a forward position. A chuck is fixed with the forward end of the fiber tip holding mechanism and includes a tapered sleeve and two or more oppositely tapered jaws.

10 Claims, 10 Drawing Sheets

(56) References Cited

U.S. PATENT DOCUMENTS

2014/0316395 A1* 10/2014 Shurgalin ............... A61B 18/22
                                                   606/13
2017/0325886 A1* 11/2017 Graham ............... A61B 18/148

* cited by examiner

LASER ENERGY DELIVERY HAND PIECE WITH DISPOSABLE OPTICAL FIBER

CROSS-REFERENCE TO RELATED APPLICATIONS

This application claims the benefit of U.S. Provisional Patent Application 62/980,354, filed on Feb. 23, 2020, and U.S. Provisional Patent Application 63/066,306, filed on Aug. 16, 2020, both incorporated herein by reference.

STATEMENT REGARDING FEDERALLY SPONSORED RESEARCH AND DEVELOPMENT

Not Applicable.

FIELD OF THE INVENTION

This invention relates to laser equipment, and more particularly to a handpiece for a medical or other type of laser.

BACKGROUND

In many medical laser systems two optical fibers are used for laser energy delivery, namely a proximal flexible fiber attached to the laser at one end and to a distal rigid optical fiber at the other which is encased in a hand piece. The latter is typically of the order of 5 cm to 10 cm in length and abuts an end of the proximal flexible fiber, but can be detached from the proximal flexible fiber and be replaced with a new distal rigid optical fiber when soiled or otherwise needing to be replaced.

For high laser energy and/or mid-IR applications, sapphire fibers are being considered as the light guide or optical fiber in the hand piece because of their high optical damage threshold, good transmission out to 3 µm and biocompatibility. Reduction in cost could be achieved if the hand piece allowed for the replacement of just this distal optical fiber.

Therefore, there is a need for a hand piece that allows for the quick interchanging of the distal optical fiber, and that itself is sterilizable or autoclavable. Such a needed invention would be relatively inexpensive to manufacture, intuitive to use, and would inhibit internal areas of the hand piece from becoming contaminated. The present invention accomplishes these objectives.

SUMMARY OF THE INVENTION

The present device is a hand piece for delivering energy from a laser to a target through a fiber tip. In some embodiments the fiber tip is included with the hand piece, and in other embodiments the fiber tip may be discarded and replaced with a new fiber tip. The laser is typically a medical laser, and the target is typically an organ of a patient in need of a therapeutic surgical procedure, or the like.

An elongated handle has a proximal end and a distal end. An axial bore traverses the handle along a longitudinal axis thereof, from the proximal end to the distal end. A fiber tip holding mechanism is fixed within the axial bore of the handle and includes a forward section fixed with the handle, a spring or other urging means, and a rear section. The rear section includes a hollow collet projecting forward therefrom and traversing the spring and an aperture of the forward section. The forward section is slidable rearward towards the rear section to compress the spring in a rear position. The spring urges the forward section forward into a forward position.

A collet chuck sleeve is fixed with the forward end of the fiber tip holding mechanism and fits around a collet with two or more jaws. The jaws are pushed forward and spring outwardly when the rear section is pushed towards the forward section such that the hollow collet forces its jaws forward and out of the sleeve. Preferably the fiber tip is a sapphire type fiber tip with a hexagonal cross-sectional shape, facilitating holding thereof by the jaws. A proximal lead fiber may be fixed through the rear section of the fiber tip holding mechanism and the hollow collet. The proximal lead fiber in some embodiments is held firm at a fiber end by a ferrule by an adhesive or by compression or crimped hold onto the proximal lead fiber. In other embodiments the end of the proximal lead fiber is fixed within the hollow collet. Alternately, the fiber tip may run the entire length of the hand piece.

As such, in use, with the forward section in the rear position and with the jaws pushed forward, the fiber tip can be inserted between the jaws and, upon release of the rear section the spring urges the jaws to clamp the fiber tip and pull the fiber tip rearwardly towards the proximal lead fiber end. When the jaws are fully retracted into the chuck sleeve and the forward section of the fiber tip holding mechanism is in the forward position, the fiber tip is held firmly within the jaws. As such, light energy from the proximal lead fiber is delivered through the fiber tip to the target.

Preferably a hand grip is fixed about at least a portion of the elongated handle. As such, to move the forward section of the fiber tip holding mechanism into the rear position, the hand grip is held in one hand while the rear section of the fiber tip holding mechanism is pushed forward to release the fiber tip from the jaws.

Preferably the hand piece further includes a hypodermic needle tip that is detachably fixed with the distal end of the elongated handle. The hypodermic needle tip includes one part of a two-part mechanical fastener at a proximal end, and a hypodermic needle at a distal end thereof. The fiber tip is slidable within the hypodermic needle.

In some embodiments, the hand piece includes an aspiration conduit fixed through the handle that is adapted to either blow a substance such as air into a space between the hypodermic needle and the fiber tip holding mechanism, or to remove a substance from the space between the hypodermic needle and the fiber tip holding mechanism.

Introducing positive pressure into the handle inhibits contaminants from entering into the elongated handle and the fiber tip holding mechanism. Similarly, an LED light bar may be fixed around the rear of the fiber tip through the fiber tip holding mechanism. Such a light bar is adapted to shine light from an LED or other light source around the fiber tip. As such, light enters the fiber tip from the sides of the fiber tip and emanates out of the distal end of the fiber tip. Preferably such light is in the visible spectrum so that the user can see where the laser beam, which may be invisible to the human eye, is aimed. Additionally, an electric heating element may be fixed adjacent to the fiber tip holding mechanism to help keep the fiber tip dry.

The present invention is a hand piece that allows for the quick interchanging of the fiber tip, and that itself is sterilizable or autoclavable. The present invention is relatively inexpensive to manufacture, intuitive to use, and inhibits internal areas of the hand piece from becoming contaminated by applying positive pressure to the aspiration conduit. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
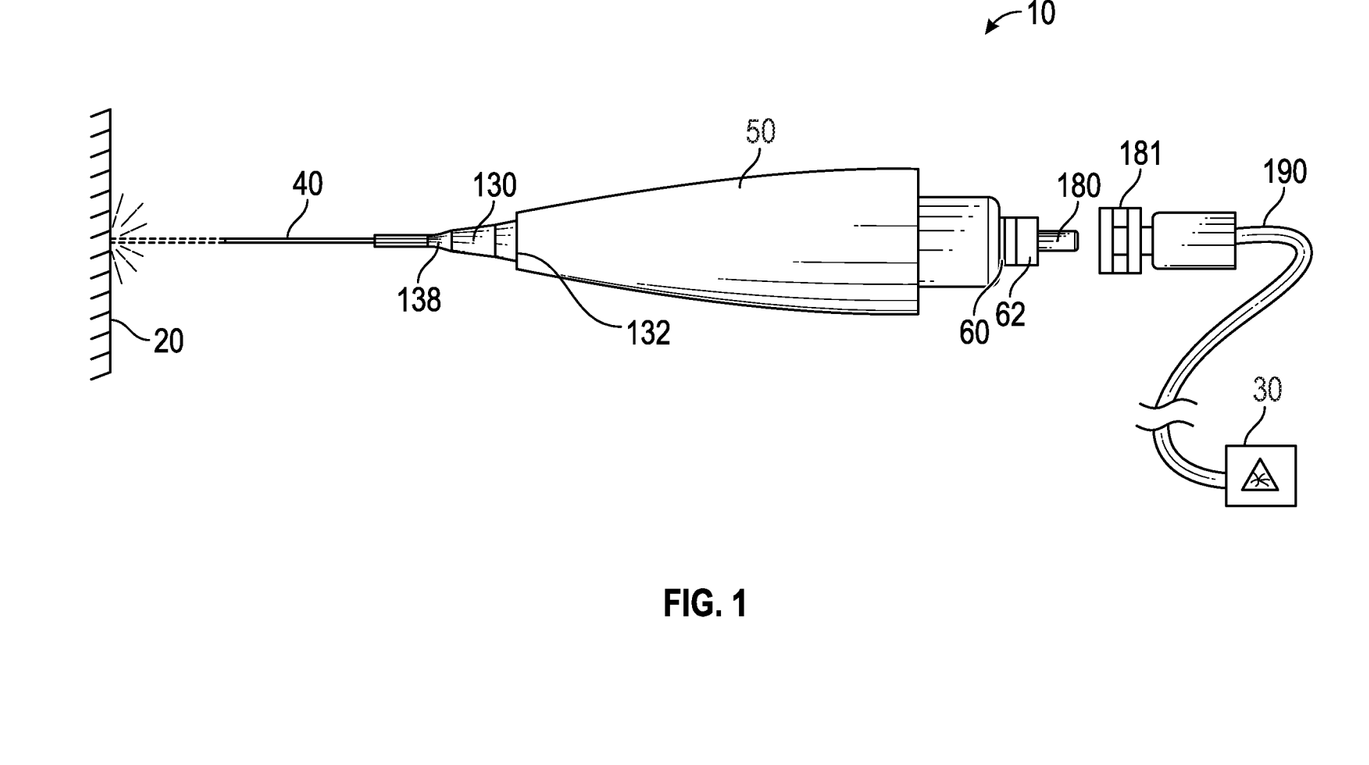
FIG. 1 is a diagram of the invention, illustrating a handpiece attachable to a laser through a proximal lead fiber extension.
Figure 2:
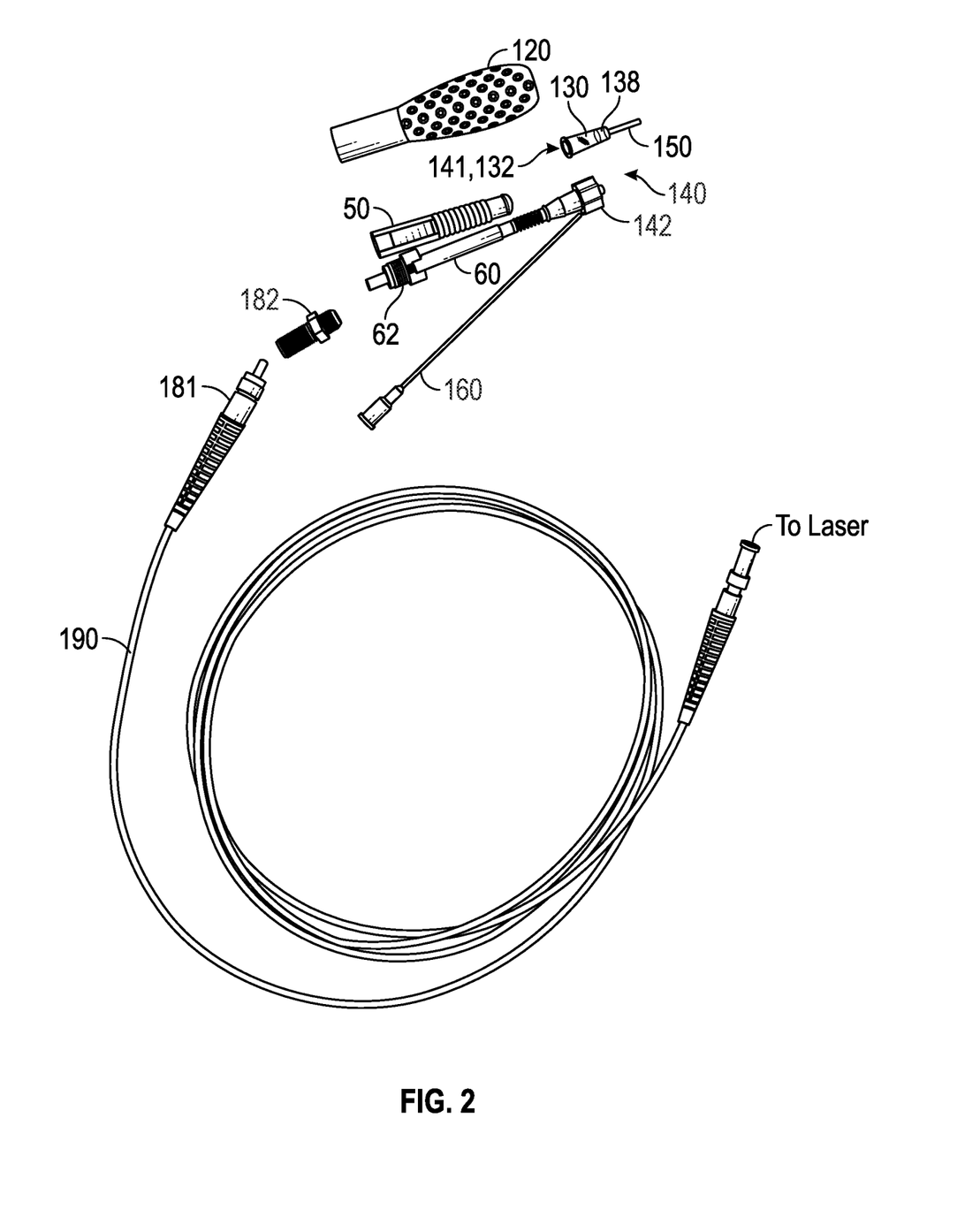
FIG. 2 is a top plan view of components of the invention.
Figure 3A:
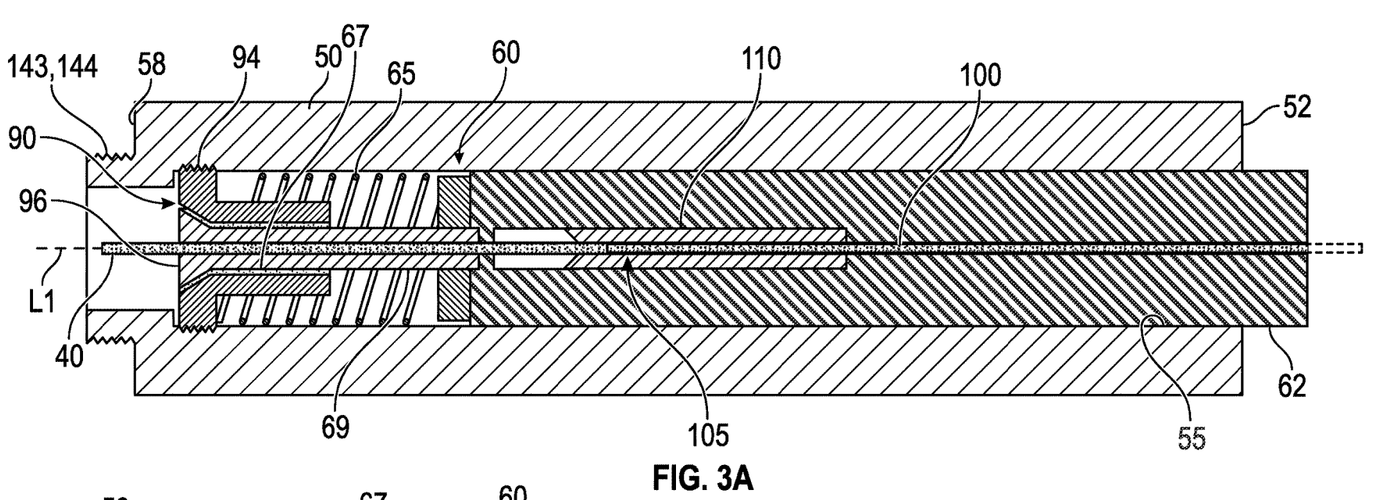
FIG. 3A is a partial cross-sectional view of an elongated handle of the invention that at least partially contains a fiber tip holding mechanism of the invention.

FIGS. 1, 2, and 3A illustrate a hand piece 10 for delivering energy from a laser 30 to a target 20 through a fiber tip 40. In some embodiments the fiber tip 40 is included with the hand piece 10, and in other embodiments the fiber tip 40 may be discarded and replaced with an after-market fiber tip 40. The laser 30 is typically a medical laser 30, and the target 20 is typically an organ of a patient in need of a therapeutic surgical procedure. As described herein, the hand piece 10 may be used manually by a medical professional (not shown), for example, or a medical robot (not shown) or other hand piece manipulation method.

An elongated handle 50 has a proximal end 52 and a distal end 58. An axial bore 55 traverses the handle 50 along a longitudinal axis $L_1$ thereof, from the proximal end 52 to the distal end 58. Preferably the elongated handle 50 is made of a rigid material such as autoclavable injection-molded plastic, metal, or the like.

Figure 3B:
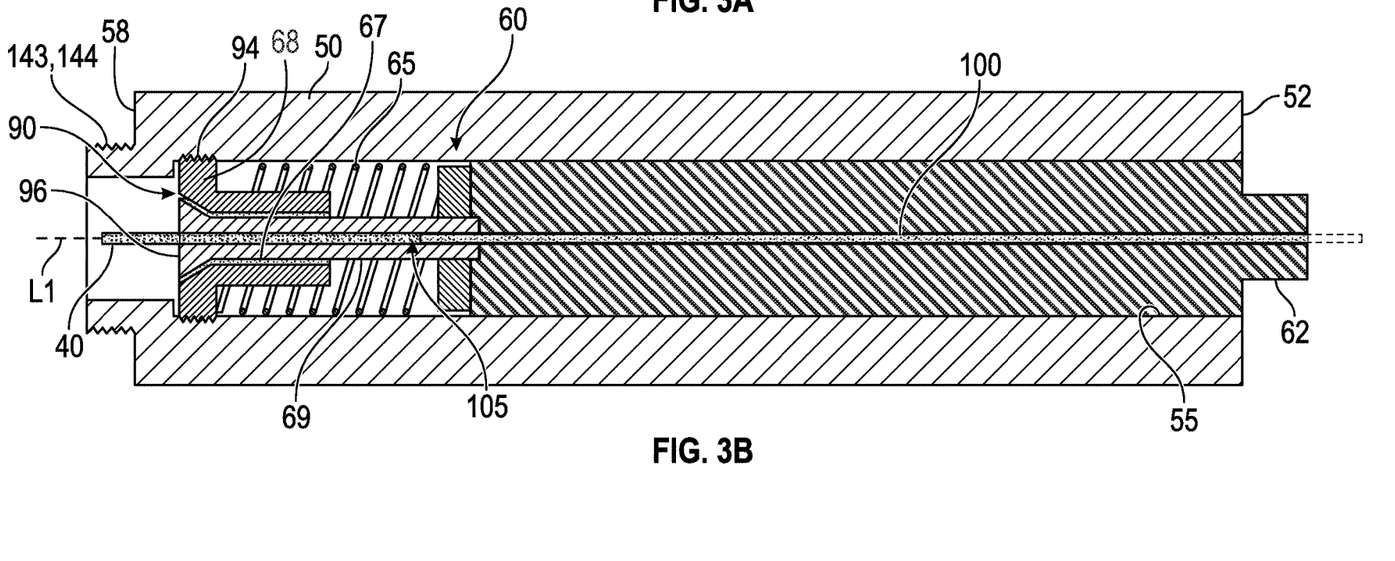
FIG. 3B is a partial cross-sectional view showing an alternate embodiment of the fiber tip holding mechanism of the invention.
Figure 3C:
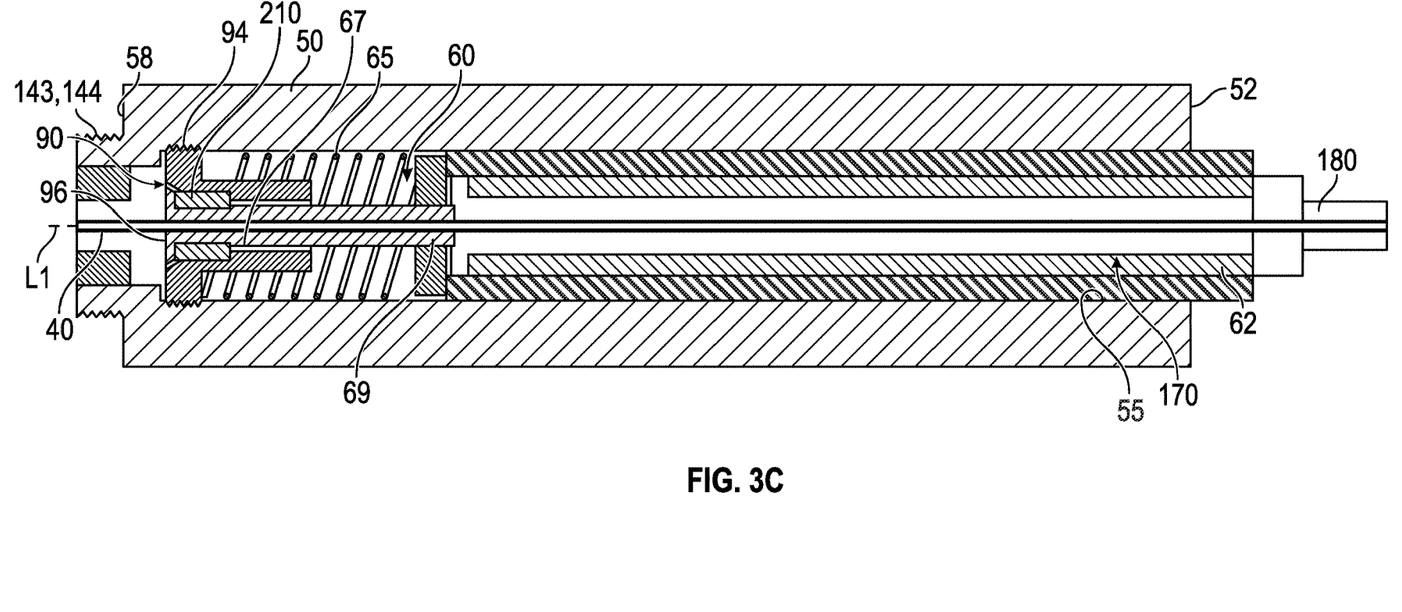
FIG. 3C is a partial cross-sectional view showing an alternative embodiment of the fiber tip holding mechanism of the invention in which the fiber tip traverses the entire length of the hand piece.
Figure 4A:
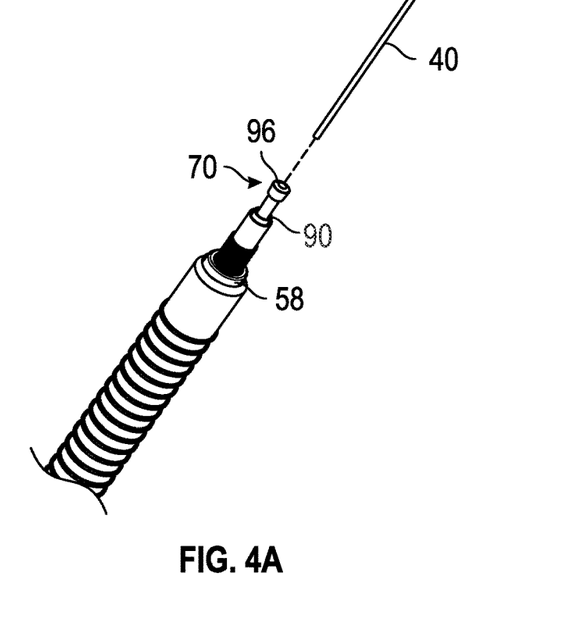
FIG. 4A is a partial perspective view of the invention with a forward section of the fiber tip holding mechanism in a rear position.
Figure 4B:
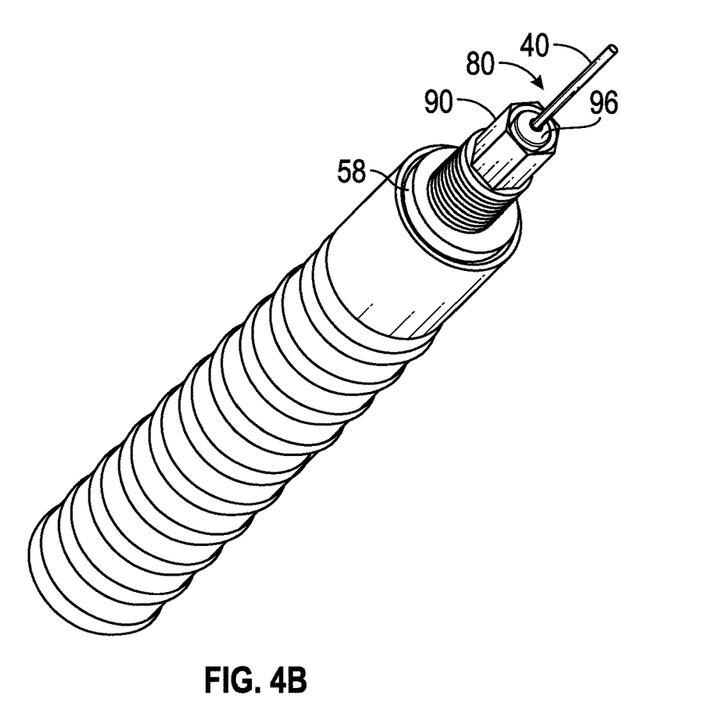
FIG. 4B is a partial perspective view of the invention with the forward section of the fiber tip holding mechanism in a forward position.
Figure 4C:
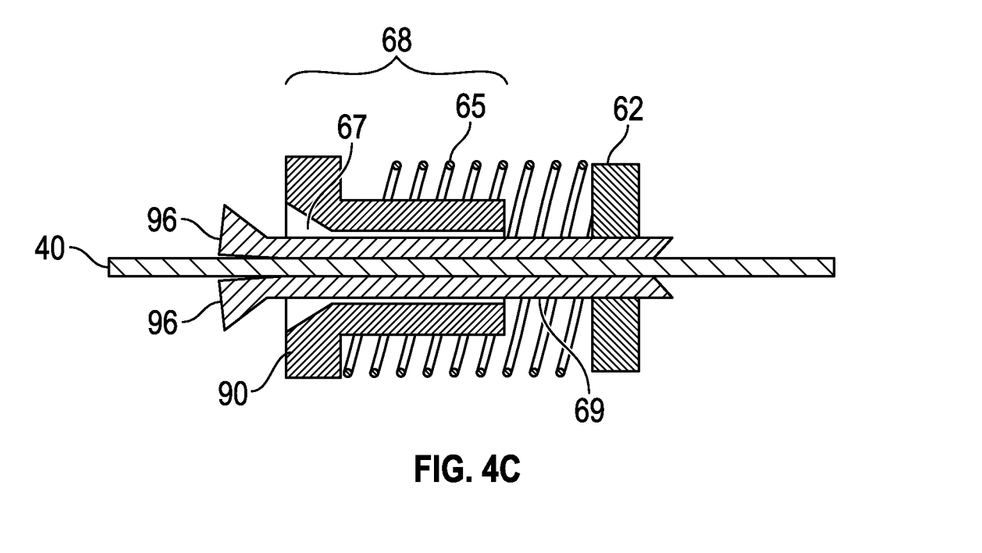
FIG. 4C is a partial cross-sectional view of a forward section, taken along a longitudinal axis of the handle, in the rear position.
Figure 4D:
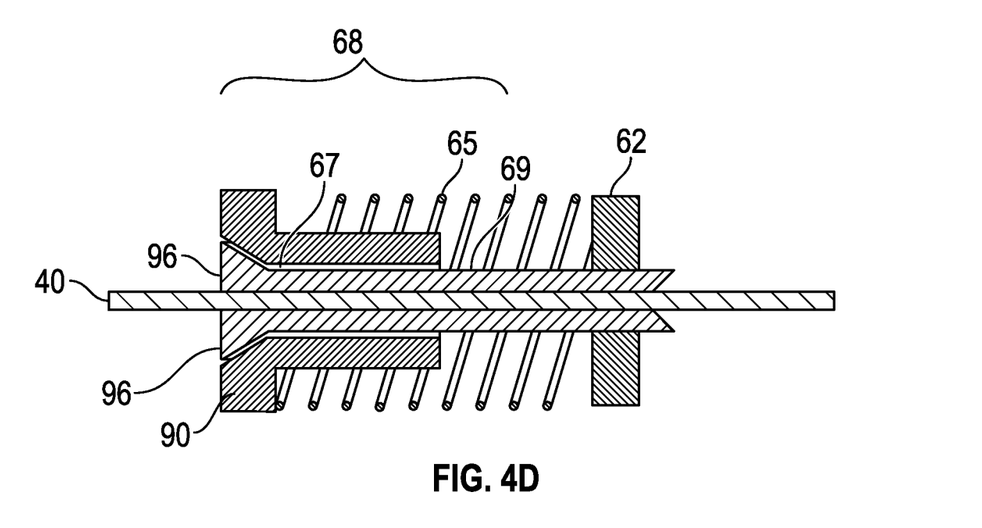
FIG. 4D is a partial cross-sectional view of a forward section, taken along a longitudinal axis of the handle, in the forward position.
Figure 4E:
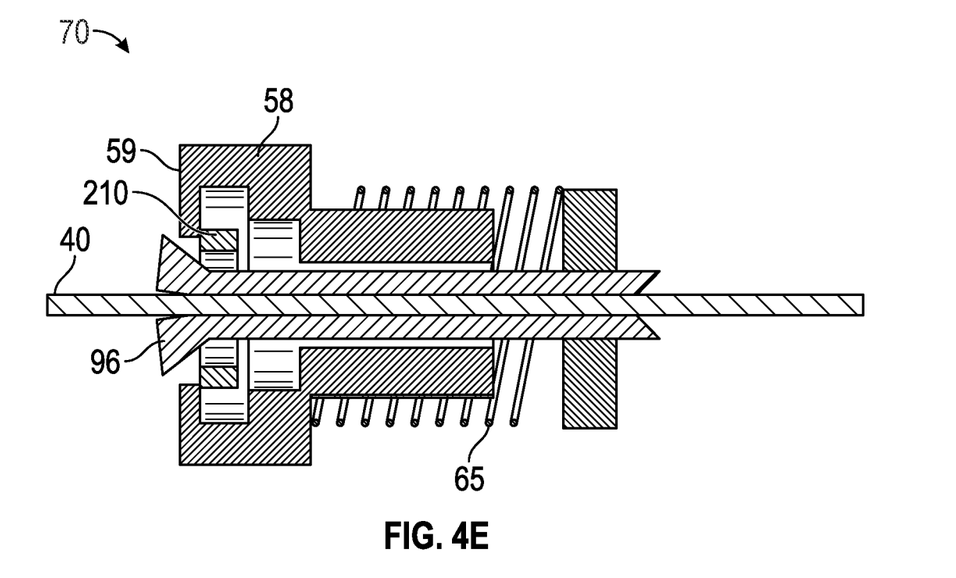
FIG. 4E is a partial cross sectional view of an alternative forward section, taken along a longitudinal axis of the handle, in the rear position.
Figure 4F:
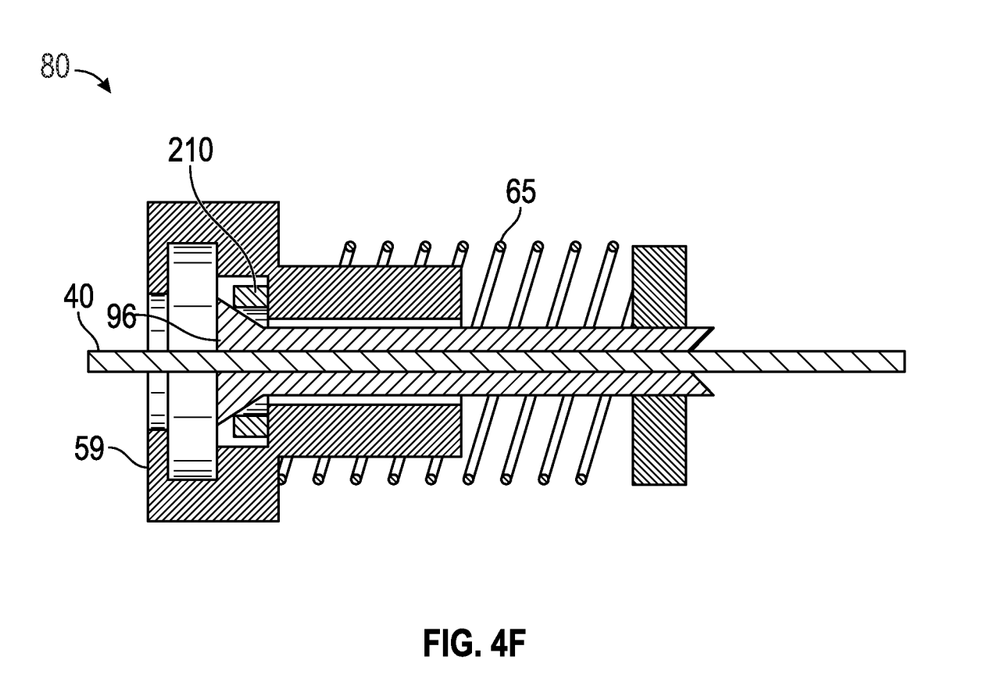
FIG. 4F is a partial cross sectional view of an alternative forward section, taken along a longitudinal axis of the handle, in the forward position.

A fiber tip holding mechanism 60 (FIGS. 3A, 3B and 3C) is fixed within the axial bore 55 of the handle 50 and includes a forward section 68 fixed with the handle 50 by threads 94, a spring 65 or other urging means, and a rear section 62. The forward section 68 includes a hollow collet 69 projecting forward therefrom and traversing the spring 65 and an aperture 67 of the forward section 68. The forward section 68 is slidable rearward towards the rear section 62 to compress the spring 65 in a rear position 70 (FIGS. 4A, 4C, and 4E). The spring 65 urges the forward section 68 forward into a forward position 80 (FIGS. 4B, 4D, and 4F).

A collet chuck sleeve 90 is fixed with the forward section 68 of the fiber tip holding mechanism 60 and fits around a hollow collet 69, with two or more tapered jaws 96. The jaws 96 are pushed forward and spring outwardly when the rear section 62 is pushed towards the forward section 68 such that the hollow collet 69 forces its jaws 96 forward and opening out of the hollow collet 69. The rear section 62 may take the form of the hollow collet 69 longitudinally slidable within the axial bore 55, and preferably the hollow collet 69 is integrally formed with the jaws 96. Preferably the fiber tip 40 is a sapphire type fiber tip 40 with a hexagonal cross-sectional shape, facilitating holding thereof by the jaws 96. Preferably the jaws 96 and the collet chuck sleeve 90 are formed from a strong metallic material.

In one embodiment (FIGS. 3A and 3B) a proximal lead fiber 100 is butt coupled to the fiber tip 40 inside the hand piece. The proximal lead fiber 100 may be fixed in a ferrule 110 as shown in FIG. 3A. Alternatively, it may be fixed in the inner sleeve 69 as shown in FIG. 3B. The point of contact 105 between the proximal fiber 100 and the fiber tip 40 is shown in both FIG. 3A and FIG. 3B. FIG. 3C shows the LED light bar or other visible light source 170 around the fiber tip 40.

As such, in use (FIGS. 4A and 4B), with the forward section 68 in the rear position 70 and with the jaws 96 pushed forward, the fiber tip 40 can be inserted between the jaws 96 and, upon release of the rear section 62 the spring 65 urges the jaws 96 to clamp the fiber tip 40 and pull the fiber tip 40 rearwardly towards the proximal lead fiber end 105. When the jaws 96 are fully retracted into the collet chuck sleeve 90 and the forward section 68 of the fiber tip holding mechanism 60 is in the forward position 80, the fiber tip 40 is held firmly abutting the end 105 of the proximal lead fiber 100. As such, light energy from the proximal lead fiber 100 is delivered through the fiber tip 40 to the target 20. When the user is finished using the hand piece 10, such as at the end of a surgical or other medical procedure, the fiber tip 40 is removed and the hand piece is then sterilized such as by autoclaving or other sterilization process.

Preferably a hand grip 120 is fixed about at least a portion of the elongated handle 50. As such, to move the forwards section 68 of the fiber tip holding mechanism 60 into the rear position 70, the hand grip 120 is held in one hand while the rear section 62 of the fiber tip holding mechanism 60 is pushed forward to release the fiber tip 40 from the jaws 96. Preferably the hand grip 120 is made from an elastomeric material, or the like. Such a hand grip 120 may be removable for sterilizing of the elongated handle 50 and other components.

Preferably the hand piece 10 further includes a hypodermic needle tip 130 that is detachably fixed with the distal end 58 of the elongated handle 50. The hypodermic needle tip 130 includes one part 141 of a two-part mechanical fastener at a proximal end 132, and a hypodermic needle 150 at a distal end 138 thereof. The fiber tip 40 is slidable within the hypodermic needle 130. Preferably one part 141 of the two part mechanical fastener 140 is a threaded bore 142, while a second part 143 of the two-part mechanical fastener is a cooperative threaded shaft 144 fixed with the distal end 58 of the handle 50. As such, the hypodermic needle tip 130 may be screwed onto the distal end 58 of the elongated handle 50.

In an alternative embodiment (FIG. 3C), the fiber tip 40 extends all the way to the rear of the fiber tip holding mechanism 60. At that point the fiber tip 40 is terminated at a fiber connector 180. An inner sleeve ring 210 (FIGS. 3C, 4E, and 4F) may be used to pinch the jaws 96 together when retracted, the inner sleeve ring 210 being retained within the handle 50 by a ring retaining flange 59 at the front end 58 of the handle 50.

Figure 6:
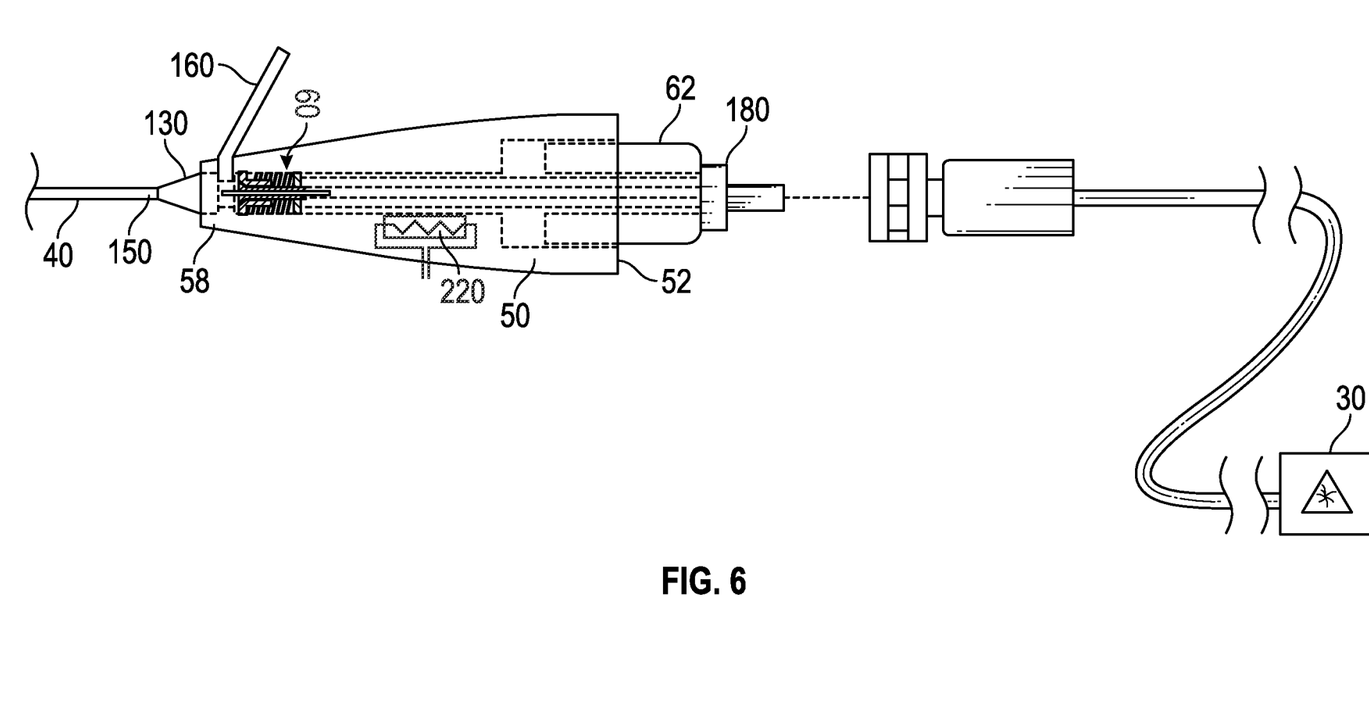
FIG. 6 is a side cross-sectional diagram showing an aspiration conduit traversing a hand grip of the invention.

In some embodiments, the hand piece 10 includes an aspiration conduit 160 (FIG. 6) fixed through the hand grip 120 that is adapted to either blow a substance such as air into a space between the hypodermic needle 130 and the fiber tip holding mechanism 60, or to remove a substance from the space between the hypodermic needle 130 and the fiber tip holding mechanism 60. Such an aspiration conduit 160 is preferably made from a rigid or semi-rigid plastic material. Further, an electric heating device 220 may be fixed on the fiber tip holding mechanism 60, whereby heat from the electric heating device 220 evaporates moisture within the elongated handle 50. Such an electric heating device 220 may be a resistance heater, infrared LED, or the like.

Preferably the proximal lead fiber 100 further includes a connector 180 at the proximal end 52 of the elongated handle 50. As such, a proximal lead fiber extensions 190 having a cooperative connector 181 can be attached thereto through a mating sleeve 182. Light traveling within the proximal lead fiber extension 190 is transmitted through the connectors 180, 181 and finally to the fiber tip 40.

Figure 5A:
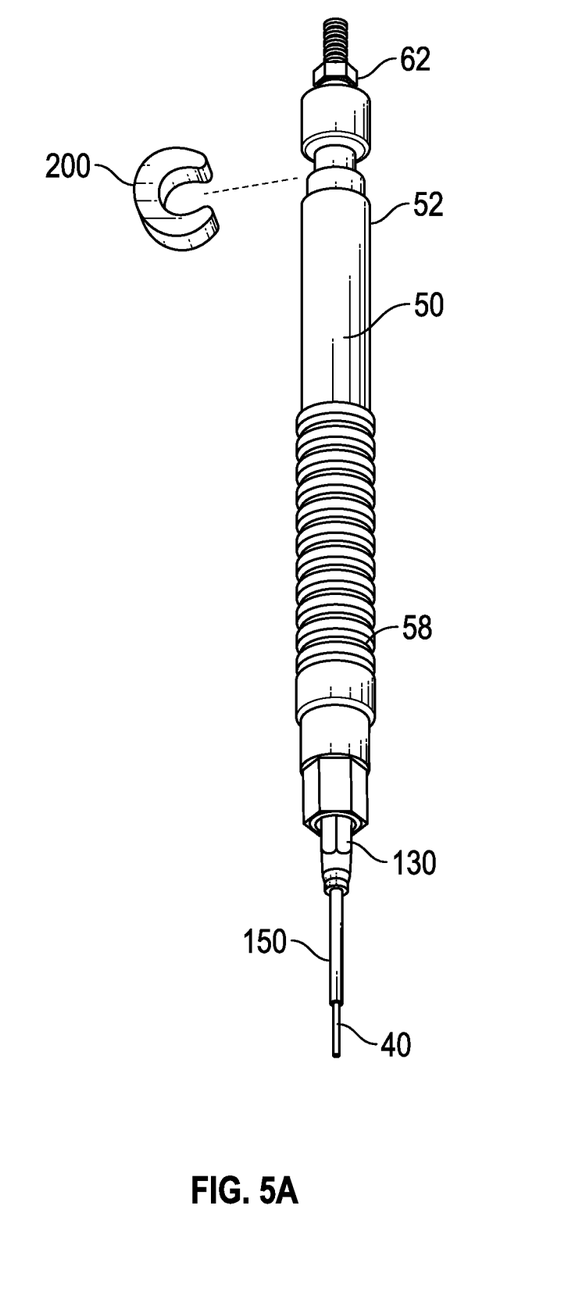
FIG. 5A is a top plan view of the handpiece showing a locking piece detached from the handpiece.
Figure 5B:
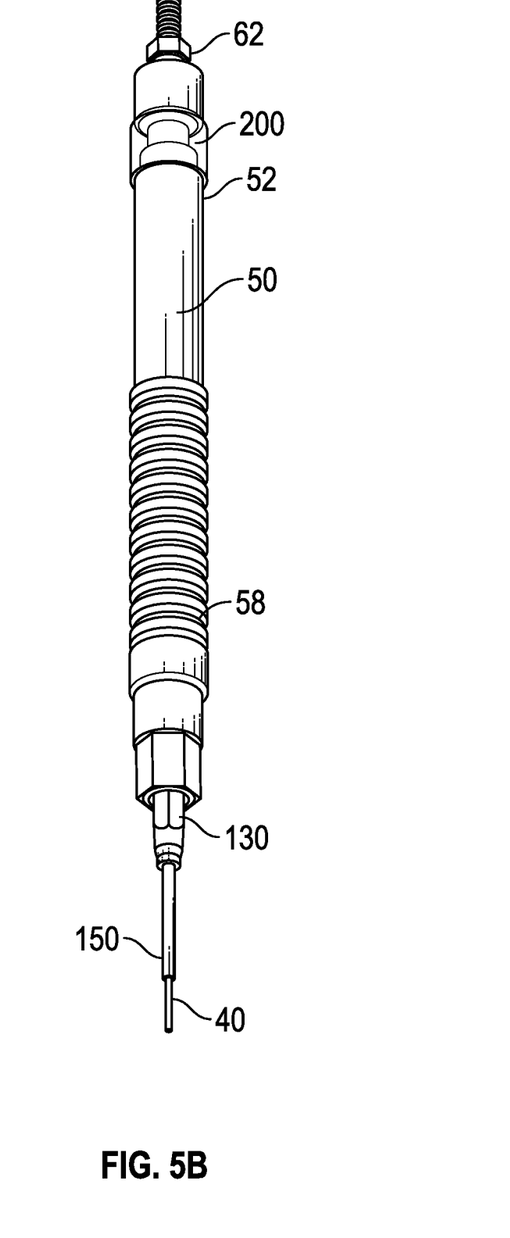
FIG. 5B is a top plan view of the handpiece showing the locking piece engaged with the handpiece to lock a fiber tip in place in the fiber tip holding mechanism.

In some embodiments, a locking piece 200 is included that, when attached to the rear section 62 of the fiber tip holding mechanism 60 (FIG. 5B) prevents the handle 50 and forward section 68 from being moved to the rear position 70, thereby locking the fiber tip 40 in place in the fiber tip holding mechanism 60. When removed (FIG. 5A), the handle 50 and forward section 68 are free to be moved to the rear position 70, allowing the fiber tip 40 to be removed and replaced.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A hand piece for delivering energy from a laser to a target through a fiber tip, comprising:
   an elongated handle having a proximal end and a distal end, an axial bore traversing the handle along a longitudinal axis thereof from the proximal end to the distal end;
   a fiber tip holding mechanism fixed within the axial bore of the handle and including a forward section fixed with the handle, a spring, and a rear section, the rear section including a hollow collet projecting forward therefrom and traversing the spring and an aperture of the forward section, the forward section slidable rearward towards the rear section to compress the spring in a rear position, the spring urging the forward section forward in a forward position;

a collet chuck sleeve fixed with the forward section of the fiber tip holding mechanism fitting around the hollow collet, comprising two or more collet chuck jaws around an axial bore, the jaws pushed forward and springing outward when the rear section of the fiber tip holding mechanism is pushed towards the forward section such that the hollow collet jaws move forward and open out of the collet chuck sleeve;

a proximal lead fiber fixed through or at the rear section of the fiber tip holding mechanism and abutting the rear of the fiber tip;

whereby with the forward section in the rear position with the jaws pushed forward, the fiber tip can be inserted therein, wherein upon release of the rear section the spring urges the jaws to clamp the fiber tip and pull the fiber tip rearwardly towards the proximal lead fiber end, whereupon when the jaws are fully retracted into the collet chuck sleeve the fiber tip is held firmly abutting the end of the proximal lead fiber.

2. The hand piece of claim 1 wherein a hand grip is fixed about at least a portion of the elongated handle;

whereby to move the forward section of the fiber tip holding mechanism into the rear position the hand grip is held in one hand and the rear section of the fiber tip holding mechanism is pushed forward to release the fiber tip.

3. The hand piece of claim 2 wherein the hand grip is made from an elastomeric material.

4. The hand piece of claim 1 further including a hypodermic needle tip is detachably fixed with the distal end of the elongated handle, the hypodermic needle tip including one part of a two part mechanical fastener at a proximal end, and a hypodermic needle at a distal end, the fiber tip slidable within the hypodermic needle.

5. The hand piece of claim 4 wherein one part of the two part mechanical fastener is a threaded bore, and a second part of the two part mechanical fastener is a cooperative threaded shaft fixed with the distal end of the handle, whereby the hypodermic needle tip may be screwed onto the distal end of the elongated handle.

6. The hand piece of claim 4 further including an aspiration conduit fixed through the elongated handle and adapted to either blow a substance into a space between the hypodermic needle and the fiber tip holding mechanism or to remove a substance from the space between the hypodermic needle and the fiber tip holding mechanism.

7. The hand piece of claim 1 further including a light source fixed with the fiber tip holding mechanism proximate the fiber tip and adapted to shine light into a side of the fiber tip, whereby light enters the fiber tip through the side thereof and emanates out of the distal end of the fiber tip.

8. The hand piece of claim 1 wherein the proximal lead fiber includes a connector at the proximal end of the elongated handle, whereby a proximal lead fiber extension having a cooperative connector can be attached thereto, light traveling within the proximal lead fiber extension being transmitted through the connectors to the proximal lead fiber and finally to the fiber tip.

9. The hand piece of claim 1 wherein an electric heating device is fixed on the fiber tip holding mechanism, whereby heat from the electric heating device evaporates moisture within the fiber tip holding mechanism.

10. The hand piece of claim 1 wherein the collet chuck sleeve comprises an outer sleeve and a slidable inner sleeve ring, whereby the outer sleeve is fixed with the handle and the slidable inner sleeve ring holds the jaws of the hollow collet and slides freely within the outer sleeve.

* * * * *